(12) United States Patent
Nakada et al.

(10) Patent No.: US 7,364,723 B1
(45) Date of Patent: *Apr. 29, 2008

(54) LIQUID PREPARATION FOR CONTACT LENSES

(75) Inventors: Kazuhiko Nakada, Kasugai (JP); Chikako Nakamura, Kasugai (JP); Tatsuya Hayashi, Kasugai (JP)

(73) Assignee: Menicon Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/088,770

(22) PCT Filed: Sep. 20, 1999

(86) PCT No.: PCT/JP99/05100

§ 371 (c)(1), (2), (4) Date: Mar. 20, 2002

(87) PCT Pub. No.: WO01/20997

PCT Pub. Date: Mar. 29, 2001

(51) Int. Cl.
*A61K 31/74* (2006.01)

(52) U.S. Cl. .................................. 424/78.04; 514/912

(58) Field of Classification Search ............. 424/78.04; 514/912

See application file for complete search history.

(56) References Cited

U.S. PATENT DOCUMENTS

| 4,361,548 A | 11/1982 | Smith et al. |
| 6,093,686 A | 7/2000 | Nakada et al. ............... 510/112 |

FOREIGN PATENT DOCUMENTS

| EP | 0942065 | 9/1999 |
| JP | 10-108899 | 4/1998 |
| JP | 10-319358 | 12/1998 |
| WO | WO 94/13774 | 6/1994 |

*Primary Examiner*—Zohreh Fay

(57) ABSTRACT

A highly safe liquid preparation for contact lenses which contains 0.3 to 50 ppm of a polyamine having recurring units of the formula (I):

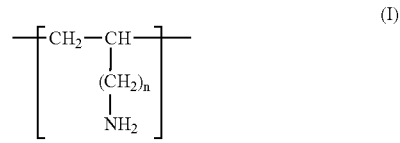

wherein n is 0 or 1, and which has a high antibacterial effect even at low concentrations.

8 Claims, No Drawings

LIQUID PREPARATION FOR CONTACT LENSES

TECHNICAL FIELD

The present invention relates to a liquid preparation for use in conjunction with contact lenses, and more particularly to a liquid preparation for contact lenses which can be suitably used, for example, for cleaning, preserving, disinfecting or rinsing contact lenses.

BACKGROUND ART

Contact lenses must be cleaned since soils such as proteins and lipids derived from lachrymal tears may adhere to the lenses. In order to prevent contamination by microorganisms such as bacteria and, it is necessary to disinfect contact lenses which have been removed from the eyes and to preserve them in an appropriate solution until they are worn again. Such treatments for cleaning, disinfection and preservation are unavoidable in safely wearing contact lenses.

However, procedures for cleaning, disinfecting and preserving contact lenses are very complicated. Moreover, several kinds of liquid preparations such as cleaning solution, disinfecting solution and preserving solution must be utilized for these treatments. The trouble and cost required for use and maintenance of contact lenses thus imposes a large burden on the users.

Multi-purpose single liquid preparations for use in conjunction with contact lenses that function for cleaning, rinsing, disinfecting and preservation necessary for the maintenance of the lenses are presently on the market here and abroad. That is to say, these liquid preparations comprise a preserving solution to which surfactant, antibacterial agent and the like are added so that all of cleaning treatment, rinsing treatment, disinfecting treatment and preservation function can be made by the single liquid preparation.

With respect to this type of the liquid preparations for contact lenses, various compounds have been heretofore investigated as antibacterial agents to be added thereto. However, these compounds all must be used in a high concentration for obtaining a practical high antibacterial activity. The use at such a high concentration may raise a problem in safety, since their toxicity is high and there is the danger of irritation to mucous membranes of the eyes and causing inflammation. Thus, investigation has been made so that a higher antibacterial effect can be obtained by the use of a smaller amount of antibacterial agent.

For example, in JP-A-6-321715, it is proposed to use a biguanide derivative in combination with a borate buffer to provide a disinfecting and preserving solution which has a low toxicity to the eyes while having a high level of antibacterial activity. In JP-A-6-504044, it is also proposed to use a biguanide derivative in combination with a tris buffer to provide a disinfecting composition for contact lenses which has substantially no irritation while having an excellent disinfecting property. However, the antibacterial effect of these liquid preparations for contact lenses is still insufficient.

Accordingly, it is an object of the present invention to provide a liquid preparation for contact lenses which can exhibit an excellent antibacterial effect or antiseptic effect while securing a high safety to the eyes.

A further object of the present invention is to provide a liquid preparation for contact lenses which enables a wearer to disinfect the contact lenses directly on the eyes without rinsing them with another rinsing solution.

DISCLOSURE OF INVENTION

The present inventors have found, as a result of making an intensive study to solve the above-mentioned problems, that when a specific polyamine is used as an antibacterial component, a sufficient disinfecting effect is exhibited even if it is used in a lower concentration than the conventional level.

Thus, in accordance with the present invention, there is provided a liquid preparation for contact lenses containing 0.3 to 50 ppm of a polyamine having recurring units of the formula (I):

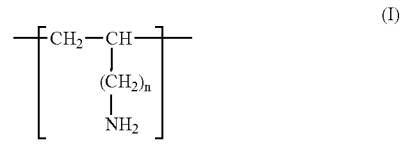

wherein n is 0 or 1.

The liquid preparation for contact lenses of the present invention is suitable for use as a shipping solution, a preserving solution, a cleaning solution and a disinfecting solution, or for use in a combination of at least two of preservation, cleaning and disinfection.

Since the polyamine which is used herein as an antibacterial agent has a high antibacterial activity and the concentration of the antibacterial agent which is necessary to exhibit the same level of the antibacterial or antiseptic effect as that of conventional disinfecting solutions for contact lenses, can be held low, the liquid preparation of the present invention can advantageously decrease the amount of the antibacterial agent and, therefore, the safety to the eyes can be further raised.

BEST MODE FOR CARRYING OUT THE INVENTION

In accordance with a preferable embodiment of the liquid preparation for contact lenses of the present invention, a higher safety to the eyes can be secured by using an aqueous medium as a medium and by adjusting the liquid preparation to a pH of 5 to 8 and an osmotic pressure of 250 to 350 mOsm/kg.

Also, in the liquid preparation of the present invention, advantageously a polyhydric alcohol is used in order to enhance the antibacterial activity of the polyamine. The concentration of the polyhydric alcohol is from 0.1 to 3 w/v %. The polyhydric alcohols are preferably dihydric and trihydric alcohols having a main chain composed of an alkylene group having 2 to 8 carbon atoms. Of these, ones having a main chain composed of an alkylene group having 2 to 5 carbon atoms is particularly advantageous in enhancing the antibacterial effect. When it is desired to prevent contact lenses from swelling, alcohols having a main chain composed of an alkylene group having 4 to 8 carbon atoms are advantageously used.

In the liquid preparation of the present invention, the polyamine is included in the aqueous medium in a concentration of 0.3 to 50 ppm. The polyamine may be used in combination with at least one other organic nitrogen-containing antibacterial agent selected as an antibacterial assistant, or an antiseptic agent, from the group consisting of quaternary ammonium compound or their polymers, a biguanide compound or its polymer, a copolymer of the quaternary ammonium compound and the biguanide compound, and an ampholytic surface active agent. These antibacterial assistants or antiseptic agents are added to the liquid preparation for contact lenses, for example, in an amount of 0.1 to 1 ppm, provided that it is preferable that the amount of the antibacterial assistant is not more than the amount of the polyamine.

In another preferable embodiment of the present invention, the liquid preparation further contains at least one member selected from the group consisting of a non-ionic surface active agent, a non-ionic or cationic thickening agent, a buffer and a chelating agent. Desired effects are imparted to the liquid preparation by the incorporation of these components. For example, a cleaning effect is imparted to the liquid preparation by the incorporation of a non-ionic surface active agent. An adequate viscosity and slippage are imparted by the incorporation of a non-ionic or cationic thickening agent, whereby can be achieved the effects that it becomes easier to clean contact lenses, soils are prevented from adhering to the lenses, a hydrophilic property is imparted to the lenses, and in case rinsing is not needed, the feel of wearing the lenses on the eyes becomes better. The incorporation of a buffer has the advantage that the pH of the preparation liquid is stabilized, whereby irritation and disorder to the eyes can be avoided. The incorporation of a chelating agent has the advantage that a chelating effect is imparted to the lenses, whereby the lenses can be protected from bad influences exerted by metal ions. Preferable examples of the buffer are hydroxyalkylamines and their derivatives. Of these, bis(2-hydroxyethyl)iminotris(hydroxymethyl)-methane is particularly preferred since it has the excellent effect of removing lachrymal soils. For the thickening agent, preferably used are saccharide derivatives, particularly cellulose derivatives, since these present no danger of exerting a bad influence on the physical properties of the lenses even in preservation for a long term.

As mentioned above, in one of the preferable embodiments of the present invention, a specific amount of a polyhydric alcohol is included in a medium composed mainly of water together with a polyamine, whereby a synergistic antibacterial or antiseptic effect is exhibited. Thus, by utilizing such a synergistic antibacterial or antiseptic effect, there is provided a useful liquid preparation for contact lenses that permits the disinfecting treatment of contact lenses more simply and easily and permits direct wear of the treated contact lenses.

The polyamines used in the present invention are polymers having recurring units of the formula (I):

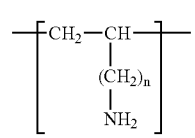

(I)

wherein n is 0 or 1. The polyamines may be homopolymers or copolymers with other radically copolymerizable monomers, particularly a hydrophilic vinyl monomer. The content of the other radically copolymerizable monomers is preferably not more than 50% by weight, more preferably not more than 30% by weight. Examples of the other radically copolymerizable monomers are, for instance, a hydroxyalkl (meth)acrylate such as hydroxymethyl (meth)acrylate, hydroxypropyl (meth)acrylate or hydroxybutyl (meth)acrylate, N-vinylpyrolidone, (meth)acrylamide, dimethyl (meth)acrylamide, and the like. Polyallylamine is prepared by polymerizing allylamine in a known manner. Polyvinylamines are prepared from vinylamine derivatives in a known manner.

From the viewpoint that a certain degree of molecular weight is needed for obtaining the desired antiseptic effect and antibacterial effect, it is desirable that the weight average molecular weight of the polyamine is not less than about 500, preferably not less than about 1,000. Also, from the viewpoint that lowering of solubility in a medium such as water may make it difficult to obtain a uniform liquid preparation and an increase in viscosity may raise a problem in handling, it is desirable that the weight average molecular weight of the polyamine is not more than about 200,000, preferably not more than about 100,000.

The content of the polyamine in the liquid preparation for contact lenses is preferably not less than 0.3 ppm from the viewpoint of sufficiently exhibiting the antiseptic and antibacterial effects of the polyamine, and is preferably not more than 50 ppm from the viewpoint of safety.

Examples of the quaternary ammonium compounds (including those in the form of salt) or their polymers which are used in the present invention as an antibacterial assistant or an antiseptic agent are, besides known cationic surface active agents, polycations such as condensates of diamines and dihalogen compounds as disclosed in Japanese Patent No. 2,550,036, benzalkonium halides, and the like. Any of them can be used so long as they are opthalmologically acceptable.

Representative cationic surface active agents are alkylammonium salts, and as the alkylammonium salts that can be used are the tetraalkylammonium salts. Examples of the tetraalkylammonium salts are, for instance, an alkyltrimethylammonium chloride such as octadecyltrimethylammonium chloride, dioleyldimethylammonium chloride, dodecyltrimethylammonium chloride, didecyldimethylammonium chloride, acylalkyltrimethylammonium chloride, tetradecyl-trimethylammonium chloride or hexadecyltrimethylammonium chloride, octadecyltrimethylammonium bromide, dioleyldimethylammonium bromide, dodecyltrimethylammonium bromide, didecyldimethyl-ammonium bromide, acylalkyltrimethylammonium bromide, tetradecyltrimethylammonium bromide, hexadecyltrimethylammonium bromide, and the like. Trialkylbenzylammonium bromides can also be used, e.g., octadecyldimethylbenzylammonium chloride and octadecyldimethylbenzylammonium bromide. Further, other opthalmologically acceptable cationic surface active agents can also be used without any restriction, e.g., alkylhydroxyalkylimidazoline quaternary salts as represented by hydroxyethylalkylimidazolinium chloride, alkylisoquinolinium salts as represented by alkylisoquinolinium bromide, alkylpyridinium salts, and amidoamines.

Representative ampholytic surface active agents which are used as an antibacterial assistant or an antiseptic agent are, for instance, alkylglycines. Examples of the alkylglycines are an alkylaminoethylglycine hydrochloride such as dodecyl(aminoethyl)glycine hydrochloride; an alkyldi(aminoethyl)glycine hydrochloride such as tetradodecyldi(aminoethyl)glycine hydrochloride or lauryldi(aminoethyl)glycine hydrochloride; an alkylpoly(aminoethyl)-glycine hydrochloride such as octylpoly(aminoethyl)glycine hydrochloride; dodecylguanidine hydrochloride; di(octylaminoethyl)-glycine hydrochloride; and the like. Any of other ampholytic surface active agents can also be used so long as they are opthalmologically acceptable, e.g., alkylbetaines such as dimethylalkylbetaine, imidazolines such as alkylimidazoline, amidobetaines, acyl-hydrolyzed collagen peptide salt, and betain acetate.

As the biguanide compounds or their polymers that can be used are known biguanide antibacterial agents such as polyhexamethylene biguanide.

The polyhydric alcohol which is used together with the polyamine in the present invention serves to enhance the antibacterial activity of the polyamine. Since the antiseptic effect and the disinfecting effect of the liquid preparation for contact lenses can be remarkably improved by the combination use of them, the liquid preparation can exhibit effective antibacterial or disinfecting effects even if the amount of the polyamine is decreased.

The polyhydric alcohol is an alcohol having at least two hydroxyl groups, and opthalmologically acceptable ones are suitably selected from known polyhydric alcohols. Of these, preferable are a dihydric alcohol such as an alkylene glycol or derivatives thereof, and a dihydric or trihydric alcohol such as glycerol or derivatives thereof. In particular, dihydric and trihydric alcohols having a main chain composed of an alkylene group having 2 to 8 carbon atoms, especially dihydric and trihydric alcohols having a main chain composed of a saturated alkylene group having 2 to 5 carbon atoms, are preferably used from the viewpoint of enhancement of antibacterial effect, e.g., ethylene glycol, propylene glycol, butylene glycol and pentylene glycol. When it is desired to prevent contact lenses from swelling, it is preferable to use dihydric and trihydric alcohols having a main chain composed of a saturated alkylene group having 4 to 8 carbon atoms, e.g., butylene glycol, pentylene glycol and hexylene glycol. The amount of the polyhydric alcohol is from 0.01 to 5 w/v %, preferably 0.1 to 3 w/v %, more preferably 0.5 to 2.5 w/v %, based on the liquid preparation for contact lenses. If the amount of the polyhydric alcohol is too small, the effect of enhancing the antibacterial activity produced by the use thereof is not sufficiently achieved. If the amount is more than 5 w/v %, the osmotic pressure of the liquid preparation itself increases and causes stimulation to the eyes and, in addition, problems arise particularly on soft contact lenses, such as change in lens size, deterioration of the feel of wear caused by change in fitting, occurrence of visual impairment and stimulation to the eyes.

It is preferable that the liquid preparation for contact lenses of the present invention is adjusted to a pH of 5 to 8, especially a pH in the vicinity of 7.0, and to an osmotic pressure of 250 to 350 mOsm/kg. If the pH and osmotic pressure are outside the above ranges, there is a possibility of giving stimulation to the eyes or causing disorder. Preferable pH adjusting agents used for such pH adjustment are sodium hydroxide and potassium hydroxide. Isotonizing agents used for adjusting the osmotic pressure include opthalmologically acceptable inorganic salts, typically sodium chloride and potassium chloride.

In order to effectively keep the pH of the liquid preparation for contact lenses within the above-mentioned range and within the range safe for the eyes, at least one buffer is usually added. The buffer is suitably selected from various kinds of conventionally known buffers. Examples of the buffers which, in particular, are safe for the eyes and have less influence on contact lenses, are acids, e.g., citric acid, malic acid, lactic acid, ascorbic acid, maleic acid, gluconic acid, phosphoric acid, boric acid, an hydroxy carboxylic acid, an amino acid such as glycine or glutamic acid, and tris(hydroxymethyl)aminomethane (Tris); their salts (e.g., sodium salts); Good-Buffer containing taurine or its derivatives; a hydroxyalkylamine such as bis(2-hydroxyethyl) imino-tris(hydroxymethyl)methane (Bis-tris); and the like. Of these, citric acid and its salts, phosphoric acid, boric acid, Good-Buffer and hydroxyalkylamines are preferred. In particular, hydroxyalkylamines, especially Bis-tris, are preferably used from the viewpoint of effectively removing lachrymal soils. The amount of the buffer is usually from about 0.01 to about 2 w/v % based on the liquid preparation for contact lenses. If the concentration of the buffer is too low, a desired buffering effect is not sufficiently exhibited. Also, even if the buffer is used in a higher amount, the pH stability is not necessarily further improved and, rather, there is a possibility of exerting a bad influence on safety such as stimulation to the eyes resulting from an increase in osmotic pressure.

Preferably the liquid preparation for contact lenses of the present invention is incorporated with a non-ionic surface active agent in order to effectively exhibit the effect of removing soils such as lipids adhering to contact lenses. The use of anionic surface active agents is not desirable since there is a danger of reacting with the polyamine used in the present invention resulting in production of a precipitate.

Any of known non-ionic surface active agents can be used so long as they have a high degree of safety to the living body and have no influence on contact lens materials. Examples of suitable non-ionic surface active agents are a polyglyceryl fatty acid ester, a polyoxyethylene alkyl ether, a polyoxyethylene-polyoxypropylene block copolymer, a polyoxyethylene-polyoxypropylene ethylenediamine, a polyoxyethylene alkylphenyl ether formaldehyde condensate, a polyoxyethylene hydrogenated castor oil, a polyoxyethylene alkylphenyl ether, a polyoxyethylene glycerol fatty acid ester, a polyoxyethylene sorbitan fatty acid ester, a polyoxyethylene castor oil, a polyoxyethylene sterol ether, a polyoxyethylene hydrogenated sterol ether, a polyoxyethylene fatty acid ester, a polyoxyethylene-polyoxypropylene alkyl ether, a polyoxyethylene lanolin alcohol, a polyoxyethylene alkylamine, a polyoxyethylene alkylamide, a polyoxyethylene alkyl ether phosphate, a polysorbate, and the like.

Of these, preferable are a polyoxyethylene alkyl ether such as polyoxyethylene lauryl ether, a polyoxyethylene-polyoxypropylene block copolymer of Pulronic type or Tetronic type, a polyoxyethylene sorbitan fatty acid ester, a polyoxyethylene alkylphenyl ether formaldehyde condensate such as Thiloxapol, a polyoxyethylene hydrogenated castor oil, a polyoxyethylene alkylphenyl ether, a polyoxyethylene fatty acid ester such as polyoxyethylene stearate, and a polysorbate.

The amount of the non-ionic surface active agent is generally from about 0.001 to about 5 w/v %, preferably from about 0.005 to about 2 w/v %, more preferably from about 0.01 to about 1 w/v %, based on the liquid preparation for contact lenses. If the amount is less than 0.001 w/v %, the cleaning effect is insufficient. If the amount is more than 5 w/v %, no increase in cleaning effect is obtained and the solution may undesirably stimulate the eyes.

The liquid preparation for contact lenses of the present invention may also include a thickener as the occasion demands. Non-ionic or cationic thickeners can be used, e.g., various gums such as heteropolysaccharides, synthetic organic polymers such as polyvinyl alcohol, poly-N-vinylpyrrolidone, polyethylene glycol, polypropylene glycol and polyacrylamide, cellulose derivatives, and starch derivatives. Such thickeners are advantageously used from the viewpoints that slippability between fingers and contact lens at the time of cleaning the contact lens with the fingers becomes better and, consequently, the cleaning property is improved. Of the thickeners which may be used, saccharide derivatives, especially cellulose derivatives, are preferably used from the viewpoint that there is no danger of exerting a bad influence on the physical properties of lens even in the preservation for a long term. Examples of such cellulose derivatives are, for instance, methyl cellulose, hydroxyethyl cellulose, hydroxypropyl cellulose, hydroxypropylmethyl cellulose and the like.

The liquid preparation for contact lenses of the present invention may also contain other additives such as a chelating agent. Any of conventionally known additives can be used so long as they are safe for the living body and have no influence on contact lens materials, and can be incorporated into the contact lens liquid preparation as occasion demands.

In particular, it is preferable to incorporate a metal chelate-forming agent into the contact lens liquid preparation of the present invention in order to prevent a metal ion such as calcium ion in the tears from being adsorbed by contact lenses, especially soft contact lenses. Examples of such a chelating agent are ethylenediaminetetraacetic acid (EDTA) and its salts such as disodium ethylenediaminetetraacetate (EDTA.2Na) and trisodium ethylenediaminetetraacetate (EDTA.3Na); citric acid, gluconic acid, tartaric acid and their salts, e.g., sodium salts. In particular, EDTA, EDTA.2Na and EDTA.3Na are preferred. The amount of the chelating agent is generally from about 0.01 to about 2 w/v % based on the liquid preparation for contact lenses. If the amount of the chelating agent is small, a sufficient effect is not expected. Even if the amount is large, the effect of the chelating agent does not further increase.

Contact lens care using the liquid preparation of the present invention is conducted in the following manner. For example, contact lenses taken off from the eyes are rubbed with the liquid preparation of the present invention, rinsed with the liquid preparation, and then immersed in the liquid preparation for a predetermined time, generally at least 30 minutes, preferably at least 2 hours, usually overnight, in a suitable container filled with the liquid preparation, thereby achieving the preservation and disinfection of the contact lenses. When the contact lenses are worn again, the lenses are taken out of the liquid preparation and worn on the eyes. Since the liquid preparation of the present invention is safe to the eyes, it is not required to rinse the lenses with physiological saline or the like and, therefore, the lenses immersed in the liquid preparation may be taken out and can be directly worn on the eyes. That is to say, if the liquid preparation for contact lenses of the present invention is used, the contact lens care can be very simply and easily carried out since all of cleaning, preservation, disinfection and rinsing of contact lenses can be achieved using only the one liquid preparation.

All kinds of contact lenses can be treated with the liquid preparation of the present invention without any restriction. For example, the liquid preparation of the present invention is applicable to all kinds of soft contact lenses such as low water-containing type and high water-containing type, and hard contact lenses, and the materials of the contact lenses and the like are not restricted upon the application of the liquid preparation.

The present invention is specifically explained by means of Examples, but it is to be understood that the present invention is not limited to these Examples.

EXAMPLES 1 AND 2 AND COMPARATIVE EXAMPLES 1 TO 3

A liquid preparation for contact lenses was prepared by dissolving polyallylamine having a weight average molecular weight of about 10,000 in water in a concentration shown in Table 1. The disinfecting test of the obtained liquid preparation was made in the following manner.

(A) Disinfecting Test

The disinfecting test and evaluation of the liquid preparation were made according to United States Pharmacopoeia 23 using *Candida albicans* IFO 1594 and *Pseudomonas aeruginosa* IFO 13275 as test microorganisms. The results are shown in Table 1, wherein the values denote Log reduction of the number of viable cells of the microorganism which were inoculated and allowed to stand at room temperature for 4 hours.

COMPARATIVE EXAMPLE 4

The procedure of Example 1 was repeated except that 1 ppm of polyhexamethylene biguanide (PHMB) was used as an antibacterial agent instead of polyallylamine. The result is shown in Table 1.

TABLE 1

| | | Log reduction | |
|---|---|---|---|
| | Concentration of | P. aeruginosa | C. albicans |
| Com. Ex. 1 | 0.12 (=1,200 ppm) | >3.04 | 4.16 |
| Com. Ex. 2 | 0.012 (=120 ppm) | >3.04 | 3.86 |
| Example 1 | 0.0012 (=12 ppm) | >3.57 | >3.87 |
| Example 2 | 0.00012 (=1.2 ppm) | >3.57 | 1.18 |
| Com. Ex. 3 | 0.000012 (=0.12 ppm) | −0.95 | −0.04 |
| Com. Ex. 4 | PHMB (1 ppm) | — | 0.46 |

(Note) PHMB: polyhexamethylene biguanide

As shown in Table 1, the concentrations of bactericidal agent in the liquid preparations of Example 1 and Comparative Example 2 are different from each other by 10 times, but the bactericidal effects thereof to *P. aeruginosa* and *C. albicans* are on the same level. Also, in case of using 1 ppm of polyhexamethylene biguanide (PHMB) which has been conventionally used as a bactericidal agent (Comparative Example 4), no sufficient bactericidal effect is obtained since the value to *C. albicans* is low. Further, if the polyamine concentration is too low (Comparative Example 3), no sufficient bactericidal effect is obtained since the values to *P. aeruginosa* and *C. albicans* are low.

INDUSTRIAL APPLICABILITY

The liquid preparation for contact lenses of the present invention has an excellent antibacterial or antiseptic effect, and can be advantageously used for the purpose of every treatment of contact lenses such as cleaning, preservation, disinfection and rinsing.

The invention claimed is:

1. A liquid preparation for contact lenses containing 0.3 to 50 ppm of a polyamine having recurring units of the formula (I):

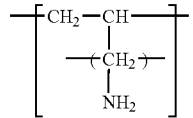

2. The liquid preparation of claim 1, which further contains at least one member selected from the group consisting of an antiseptic agent, a chelating agent, a buffer, an isotonizing agent, a thickener, a surface active agent and an antibacterial assistant.

3. The liquid preparation of claim 1, which is used as a shipping solution, a preserving solution, a cleaning solution or a disinfecting solution, or for at least two purposes selected from preservation, cleaning and disinfection.

4. The liquid preparation of claim 1, which further contains a surface active agent selected from the group consisting of a non-ionic surface active agent, a cationic surface active agent and an ampholytic surface active agent.

5. A process for protecting contact lenses from bacterial growth, comprising:
contacting a contact lens with a liquid preparation containing 0.3 to 50 ppm of a polyamine having recurring units of the formula (I):

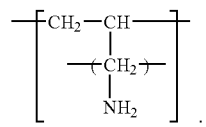

6. A process according to claim 5, wherein the liquid further contains at least one member selected from the group consisting of an antiseptic agent, a chelating agent, a buffer, an isotonizing agent, a thickener, a surface active agent and an antibacterial assistant.

7. A process according to claim 5, wherein the lens is maintained in the liquid for use as a shipping solution, a preserving solution, a cleaning solution or a disinfecting solution, or for at least two purposes selected from preservation, cleaning and disinfection.

8. A process according to claim 7, wherein the liquid further contains a surface active agent selected from the group consisting of a non-ionic surface active agent, a cationic surface active agent and an ampholytic surface active agent.

* * * * *